US00PP24312P2

(12) United States Plant Patent
Hurd

(10) Patent No.: US PP24,312 P2
(45) Date of Patent: Mar. 11, 2014

(54) ***SALVIA* PLANT NAMED 'SWEET 16'**

(50) Latin Name: *Salvia pratensis*
Varietal Denomination: Sweet 16

(75) Inventor: Kevin A. Hurd, Chicago, IL (US)

(73) Assignee: Walter Gardens, Inc., Zeeland, MI (US)

( * ) Notice: Subject to any disclaimer, the term of this patent is extended or adjusted under 35 U.S.C. 154(b) by 171 days.

(21) Appl. No.: 13/385,335

(22) Filed: Feb. 14, 2012

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Kent L Bell

(57) ABSTRACT

A new and distinct cultivar of *Salvia* plant named 'Sweet 16' characterized by its large deep fuchsia-pink flowers densely arranged in whorls, with compact habit and branched scapes and strong vigorous growth rate.

1 Drawing Sheet

Botanical denomination: *Salvia pratensis.*
Cultivar designation: 'Sweet 16'.

BACKGROUND OF THE INVENTION

The present invention relates to a new and distinct cultivar of ornamental Sage plant hereinafter referred to by the cultivar name *Salvia* 'Sweet 16' or as the new plant. The new plant is the result of an open pollination in the summer of 2006 from *Salvia* 'Eveline' U.S. Plant Pat. No. 14,905 as the female (seed) parent. The male (pollen) parent is unknown. The new *Salvia* was selected from a cultivated state at a nursery in Zeeland, Mich., USA during evaluations in the summer of 2008 by the inventor, Kevin A. Hurd, as the one unique plant best fitting the goals of darker flowers and more compact habit. The plant was then further evaluated with asexual propagation by tip cuttings. The resulting plants of *Salvia* 'Sweet 16' from asexual propagation taken at the same nursery in Zeeland, Mich. have been found to be true to type and stable in successive generations.

SUMMARY OF THE INVENTION

Plants of the new *Salvia* have not been observed under all possible environmental conditions. The phenotype may vary somewhat with variations in environment such as temperature, nutrition and light intensity without, however, any variance in genotype.

*Salvia* 'Pink Delight' U.S. Plant Pat. No. 14,965 and *Salvia* 'Eveline' are comparible *Salvia pratensis* hardy sages. The new plant can most closely be compared to the seed parent *Salvia* 'Eveline' which has a lighter flower color, is about 10 cm taller in flower and begins flowering about one week after 'Sweet 16'. Compared with 'Pink Delight' the new plant has flowers that are much deeper in color. *Salvia* 'Endless Love' U.S. Plant Pat. No. 21,707 has a *Salvia verticillata* background and flowers on whorled scapes that are more purple less pink and smaller in size. The new plant can also be compared to *Salvia* 'Sensation Rose' U.S. Plant Pat. No. 18,230 which is from *Salvia nemerosa* and is shorter in habit and has a smaller flower that is more purple and less pink than 'Sweet 16'. *Salvia* 'Sweet 16' has larger flowers that are more pink than other *Salvia nemerosa* type sages consisting of 'Flosaldblue' U.S. Plant Pat. No. 21,297, 'Florsalwhite' U.S. Plant Pat. No. 21,243, 'Sal Card 07' U.S. Plant Pat. No. 20,184, 'Sensation Rose' U.S. Plant Pat. No. 18,230 ,'Pink Friesland' U.S. Plant Pat. No. 18,152, 'Rhapsody in Blue' U.S. Plant Pat. No. 15,148 and 'Haeumanarc' U.S. Plant Pat. No. 13,322 (more often recognized in the trade as 'Marcus'). *Salvia nemerosa* plants have flowers closely congested on scapes and not on verticils. *Salvia* 'Madeline' U.S. Plant Pat. No. 20,456 (another hardy perennial sage) has a background with *Salvia hians* and a two-tone blue and white flower also on verticils.

These traits have been repeatedly observed and are determined to be the unique characteristics of *Saliva* 'Sweet 16.' The following characteristics in combination distinguish *Saliva* 'Sweet 16' as a new and distinct cultivar:

1. Large deep fuchsia-pink flowers densely arranged in whorls.
2. Compact habit and branched scapes.
3. Strong and vigorous growth habit.

BRIEF DESCRIPTION OF THE DRAWINGS

The photographs of the new plant demonstrate the unique traits and the overall appearance of *Salvia* 'Sweet 16'. The colors are as accurate as reasonably possible with color reproductions. Variation in ambient light spectrum, source and direction may cause the appearance of minor variation in color. The plant used in the photographs was a two-year old plant grown in a covered greenhouse in Zeeland, Mich. with 50% artificial shade and supplemental water and fertilizer when needed. No growth regulators have been used.

FIG. 1 shows a close-up of the flower scape with the buds and unique flower petal color.

DETAILED BOTANICAL DESCRIPTION

The following descriptions and color references except where common dictionary terms are used are based on the 2001 edition of The Royal Horticultural Society Colour Chart. *Salvia* 'Sweet 16' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a nursery in Zeeland, Mich. Plants were given supplemental water and fertilizer but no plant growth regulators were used.

Botanical classification: *Salvia pratensis*.

Parentage: *Salvia* 'Eveline' (female or seed parent) times unknown male or pollen parent.

Plant habit: Hardy herbaceous perennial; multi-stemmed, with foliage mostly basal, and flowers in several verticils on branched upright racemes displayed above foliage; about 60 cm tall in flower with flower scapes about 50 cm wide at the fullest point; foliage about 30 cm tall and 45 cm wide.

Propagation: By herbaceous tip cuttings; time to produce rooted stems about two weeks.

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependant on age and soil type, from cream to dark tan in color.

Foliage: Opposite, simple, rugose, lanceolate with acute apex and base cordate to auriculate with lobes sometimes overlapping; margin crenate; pubescent both surfaces; size to about 20.0 cm long and 10.0 cm across, average about 14.0 cm long and 6.0 cm across; faint sage fragrance.

Foliage color: Adaxial surface between RHS 137A and RHS 136A; abaxial surface nearest RHS 137C.

Venation: Reticulate; impressed on adaxial side and ridged on abaxial side; color adaxial side between RHS 138D and RHS 139D in midrib and main veins and secondary veins gradually darkening to nearest RHS 137A toward leaf margin; abaxial color midrib between RHS 146D and RHS 145A and main veins and secondary veins gradually darkening to nearest RHS 137C.

Petiole: Concave adaxial side, convex abaxial side, heavily pubescent; average 8.5 cm long and 5.0 mm wide at base.

Petiole color: Both surfaces between RHS 138B and RHS 138C.

Flower description: Perfect, bilabiate, verticillate with flowering generally beginning at lower verticils but not all flowers at each verticil opening at the same time giving the effect of a scape being in continuous flower for long periods; projected at about 90 degree angle to stem; self-cleaning, petals not persistent; flowering beginning early summer for about five weeks and repeating if scapes removed.

Flower longevity: About five days on the plant or as cut flower.

Fragrance: None detected.

Flower buds one to two days prior to anthesis: About 1.8 cm long, 8.0 mm tall and 3.0 mm wide; shape is rounded on top and slightly concave below; pubescent.

Bud color: Petals between RHS N78A and RHS N78B.

Flowers: About 2.4 cm long, 2.0 cm tall and 5.0 mm wide.

Petals: Bilabiate corolla; upper petal hooded, with notched apex and base fused with labium, about 2.4 cm long, 1.0 cm tall and 5.0 mm across; labium (lower petal) consisting of four lobes, two proximal lobes about 3.0 mm long and 2.0 mm wide at base with acute apex, two distal lobes about 4.0 mm long 4.0 mm wide with a 1.0 mm notch between; petals both minutely pubescent outside, glabrous inside.

Petal color: Upper petal nearest RHS N78C inside and outside; labium between RHS N78C and RHS N78B in both inner and outer surfaces.

Androecium: Two, contained within hood petal except when triggered by pollinator.

*Stamen*.—Fused about 6.0 mm from base of petals; curved around inside of hooded petal with 1.0 mm trip mechanism at base; color whiter than RHS 155D at base and lighter than RHS 77D before stamen.

*Anther*.—Oblong, about 3 mm long and 1 mm diameter, dorsifixed; nearest RHS N186C.

*Pollen*.—RHS 17D.

Gynoecium: One, curved around inside of hooded petal.

*Style*.—About 2.4 cm long and less than 1 mm diameter; color white, lighter than RHS 155D darkening rapidly to RHS N79B before stigma.

*Stigma*.—Split in two in the terminal 2.0 mm; nearest RHS N79B; Ovary; superior; color between RHS 145A and RHS 138B.

*Fruit*.—Nutlet, up to four at base inside calyx; rounded, about 1.0 mm diameter; color darker than RHS 200A.

Calyx: Five sepals, three upper and two lower, campanulate, apex acute; fused base; upper and lower sets fused to within 1.0 mm of apex and cleft about 3.0 mm deep between upper and lower sets.

Calyx color: Abaxial between RHS 191A and RHS 138A with undertones of RHS 183D with nearest RHS 191A especially in the upper portions of the scape; adaxial nearest RHS 138B with darker veins of RHS 137B.

Bracts: Each verticil subtended by two opposite bracts; apex acute, base attenuate, shape nearly cordate; minutely pubescent below and glabrous above; bract size up to 1.5 cm long and 1.0 cm wide, decreasing distally; color of both surfaces nearest RHS 138B with center base and proximal half of main vein nearest RHS 138D.

Peduncles: About 18 per plant; strong; mostly upright, up to 60 cm tall and 5.0 mm across, square in cross section; finely pubescent; branches mostly upright at lower nodes with branches about 15.0 cm long and 3.0 mm across.

Peduncle color: Nearest RHS 144A with tinting of nearest RHS 187B concentrated in the distal portions with more light, and at the nodes.

Pedicels: About 2.0 mm long and 1.0 mm diameter; pubescent; horizontal to about 20 degrees above horizontal.

Pedicel color: Nearest RHS 138B.

Disease and pest resistance: Plants of *Salvia* 'Sweet 16' perform best with adequate moisture and good drainage; are hardy from USDA zone 3 to 8; resistant to diseases and pests beyond that common to *Salvia* has not been noted.

It is claimed:

1. A new and distinct *Salvia* plant named 'Sweet 16' as herein described and illustrated useful for landscaping as a specimen plant, en masse or as a cut flower.

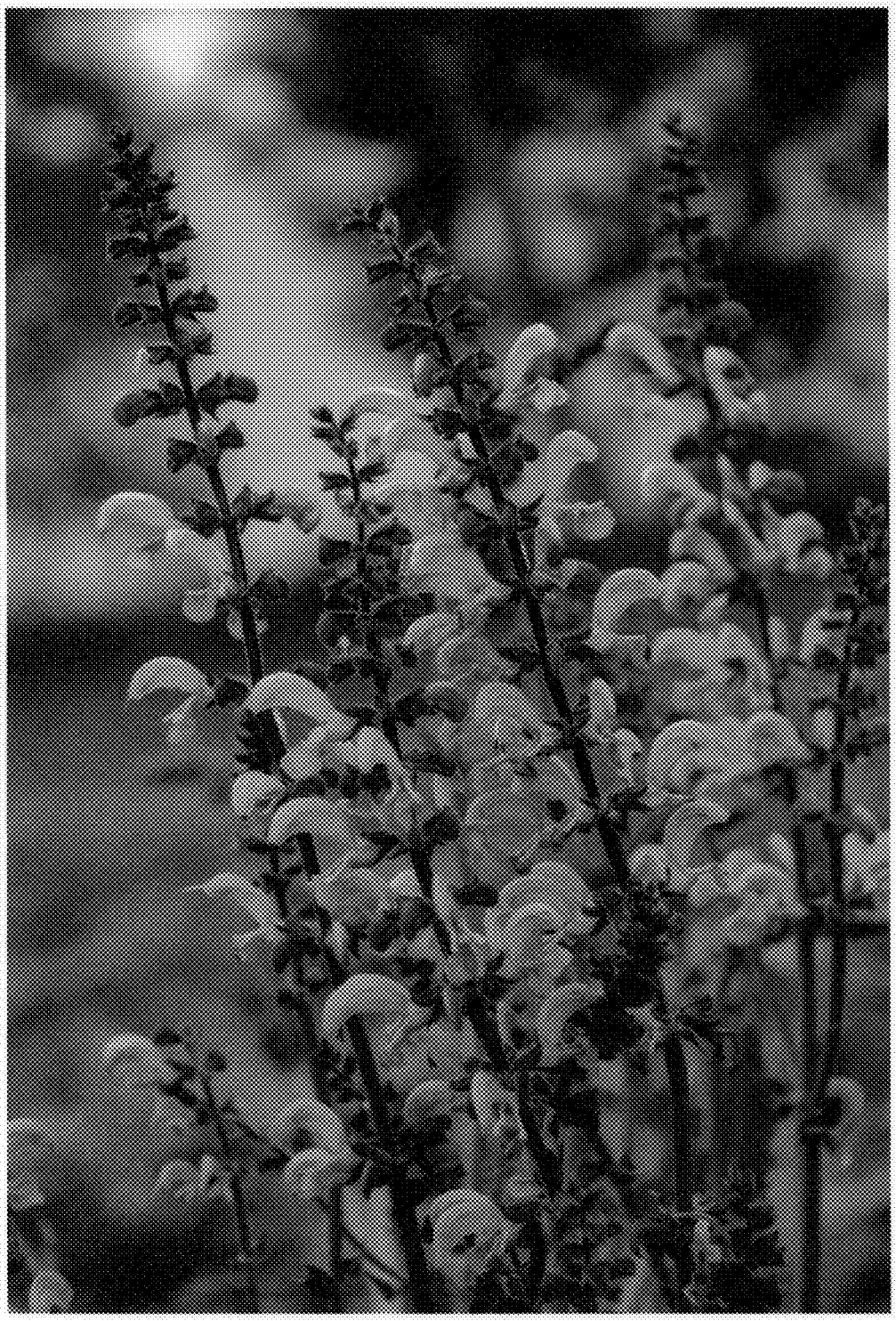

* * * * *